United States Patent [19]

Kulprathipanja et al.

[11] Patent Number: 5,488,156
[45] Date of Patent: Jan. 30, 1996

[54] PREPARATION OF A HEAT-STABLE LACTIC ACID

[75] Inventors: Santi Kulprathipanja, Inverness; Gregory F. Maher, Aurora; Thomas W. Lorsbach, La Grange, all of Ill.

[73] Assignee: UOP, Des Plaines, Ill.

[21] Appl. No.: 363,662

[22] Filed: Dec. 23, 1994

[51] Int. Cl.⁶ .................................................... C07C 51/42
[52] U.S. Cl. ............................................. 562/580; 562/589
[58] Field of Search ...................................... 562/580, 589

[56] References Cited

U.S. PATENT DOCUMENTS

| | | | |
|---|---|---|---|
| 2,885,436 | 5/1959 | Wangel | 260/535 |
| 3,202,705 | 8/1965 | Powell et al. | 260/535 |
| 4,334,095 | 6/1982 | Baniel | 562/584 |

OTHER PUBLICATIONS

CA 119:269073 (1991).
CA 95:203332 (1981).

Primary Examiner—José G. Dees
Assistant Examiner—Barbara S. Frazier
Attorney, Agent, or Firm—Thomas K. McBride; Eugene I. Snyder

[57] ABSTRACT

Lactic acid formed via fermentation generally is susceptible to the development of color bodies when heated to temperatures of approximately 180° C. and above. Color development appears to result from carbonization of small amounts of carbohydrates. Consequently a heat-stable lactic acid may be produced by subjecting an aqueous solution of lactic acid to temperatures between about 180 and 230° C. for a time sufficient to carbonize the carbohydrates, with subsequent removal of the color bodies using standard decolorants such as activated charcoal. Heat treatment may be applied either directly to the broth or to an aqueous solution resulting from one or more processing steps applied to the fermentation broth.

12 Claims, No Drawings

PREPARATION OF A HEAT-STABLE LACTIC ACID

BACKGROUND OF THE INVENTION

Lactic acid is used as a food acidulant and flavoring and in pharmaceuticals, plastics, textiles and other industrial formulations. The increased use of food and pharmaceutical products formulated with lactic acid has been primarily responsible for growth of world wide production of lactic acid to about 300 million pounds per year which is expected to continue in the future.

Lactic acid is produced by a submerged culture fermentation process which employs molasses, potatoes or starch as feed and a microorganism such as *Lactobacillus del brueckii, L. bulgarcius,* or *L. leichnanii.* The fermentation product also contains carbohydrates, amino acids, proteins and salts in addition to lactic acid, necessitating a more or less elaborate separation and purification scheme.

In the customary separation of lactic acid, the calcium salt is precipitated. The resulting calcium lactate is filtered to remove heavy metal and some organic impurities. Lactic acid is subsequently regenerated using $H_2SO_4$ and is separated from the precipitated $CaSO_4$, as by filtration, and the resulting crude lactic acid is then further purified by carbon treatment and sodium ferrocyanide to remove additional organic impurities and heavy metals, respectively. After filtration, the lactic acid is contacted with an ion exchange resin to remove trace ions. The purification process is complex and high purity is difficult to obtain.

More recently lactic acid has been used as a monomer in the preparation of, for example, poly(lactic acid) and copolymers such as those with glycollic and methylglycollic acid, polymers which are of increasing interest because of their biodegradability. For example, polymers and copolymers of lactic acid have been used as microencapsulants for the controlled release of pharmaceutically active agents; as the polymer degrades it effectuates a controlled release of the encapsulated drag. A drug delivery device even can be surgically implanted where the device is designed to release the drug slowly over extended periods of time. Polymers and copolymers of lactic acid also are used medically as, for example, sutures and wound closing staples.

The medical uses of the polymers and copolymers of lactic acid require high monomer purity. But in addition to the medical uses of lactic acid polymers and copolymers there is widespread interest in the use of these polymers and copolymers as commercial biodegradable polymers in, for example, containers for the fast food industry. Although the purity of monomeric lactic acid in the strictest sense of the word may not be of prime importance for commercial products in non-medical applications, the appearance of the polymeric product is of great importance. In particular, it is important that commercial polymers not be discolored. This often is a problem because polymers are prepared at high temperatures (approximately 200° C.) where commercial lactic acid frequently shows low heat stability in the sense of developing color bodies. In fact, for the preparation of a colorless lactic acid polymer or copolymer it is necessary that lactic acid remain colorless upon being heated at 180° C. for 3 hours. Even where the lactic acid is subjected to more or less elaborate purification schemes the resulting purified lactic acid still may not exhibit the requisite heat stability and hence may be unsuitable in the preparation of lactic acid polymers and copolymers.

Confronted with the problem of producing a heat-stable lactic acid, we noted that lactic acid produced via fermentation almost invariably developed color when heated, regardless of the purification methods used. This rather remarkable observation of susceptibility to color development being independent of the purification process applied led us to surmise that color development was associated with trace amounts of carbohydrates in the lactic acid sample which underwent carbonization upon heating. Were this hypothesis correct, then a heat-stable lactic acid could be readily prepared by subjecting an aqueous solution of lactic acid to a sufficient heat treatment to develop color bodies via carbonization of carbohydrates with subsequent removal of the color bodies. Since no uncarbonized carbohydrates would remain at this point, lactic acid subsequently isolated would manifest the requisite heat stability. In fact, this hypothesis proved correct. What was particularly gratifying was the observation that heat stability did not require that the heat treatment be applied at a particular stage in lactic acid purification, but rather that heat treatment could be effected at various stages in the purification process. This is not to say that all variants are equally effective, but rather that there is a wide range of options within a general lactic acid purification scheme where heat treatment can be incorporated ultimately to afford a heat-stable lactic acid.

SUMMARY OF THE INVENTION

The purpose of this invention is to afford a heat-stable lactic acid where the latter is produced via fermentation. An embodiment comprises heating an unpurified aqueous solution of lactic acid, whether the fermentation broth itself or an aqueous solution resulting from subsequent treatment of a fermentation broth, at a pH less than 3 or greater than 8.5 at a temperature between about 180° and 230° C. for a time sufficient to carbonize the carbohydrates dissolved in the aqueous solution. In a more specific embodiment the lactic acid solution contains between 8 and 20 weight percent lactic acid. In another specific embodiment the temperature is maintained in the interval between about 190° and 220° C. Other embodiments and variants will be apparent from the ensuing description.

DESCRIPTION OF THE INVENTION

Necessity is the mother of invention, and our necessity was to find a method of preparing heat-stable lactic acid initially produced via fermentation. Adopting the hypothesis that the development of color bodies was associated with carbonization of carbohydrates present in lactic acid at very low concentrations, we reasoned that deliberate carbonization of these carbohydrates via a suitable heat treatment with subsequent removal of the color bodies would afford lactic acid manifesting the requisite heat stability. In fact this surmise proved correct and is the basis of our invention Lactic acid currently is produced on an industrial scale either by fermentation or chemical synthesis. In recent years production by fermentation has increased as the market demand for lactic acid has increased. The fermentation medium contains, in addition to soluble proteins and salts as bacterial nutrients, starches and starch degradation products as the substrate for bacterial fermentation. Homolactic fermentation is preferred, as it leads to smaller amounts of other fermentation products, such as acetic acid, ethanol, and so on, than does heterolactic fermentation and generally produces L - or racemic lactic acid. The Lactobacilli are anaerobic organisms so that fermentation, too, is anaerobic.

When fermentation is complete the broth is heated to kill the microorganisms and then acidified to low pH, generally under 2. Precipitated materials are removed by filtration and the filtrate is decolorized with activated charcoal. After ion exchange, the filtrate is concentrated to contain approximately 80 weight percent lactic acid. For pharmaceutical grade lactic add additional purification steps are necessary, such as liquid-liquid extraction, by steam distillation, by esterification followed by distillation and hydrolysis, by calcium salt formation and re-release of the acid, or by reverse osmosis. See *Ullmann's Encyclopedia of Industrial Chemistry*, 5th ed., V. A15, pp. 100–101. More recently a purification process based on adsorption using a weakly basic anionic polymeric adsorbent has been taught; see U.S. 5,068,418.

Our invention of producing a heat-stable lactic acid is applicable to any method of isolating lactic acid from the fermentation broth, whether applied to the crude broth or an aqueous solution of lactic acid resulting from processing of a fermentation broth. This characteristic is quite desirable, for it lends flexibility in producing a heat-stable lactic acid without the necessity of changing the particular parent processing method in any substantial fashion. Our invention is typically applied to aqueous solutions containing from 8 to about 20 weight percent lactic acid, and even more usually to solutions containing between about 10 and about 12 weight percent lactic acid.

The process which is our invention is the application of heat treatment to a lactic acid aqueous solution to afford a heat-stable lactic acid product. What is meant by a "heat-stable lactic acid" is that an 88 weight percent aqueous lactic solution heated to 180° C. for 3 hours develops no color as determined visually. Although such a standard is somewhat subjective it is currently the industry-accepted one.

The process which is our invention is applicable to any method of purification and isolation of lactic acid. Consequently, many variants are within the basic method which requires heating the aqueous solution of lactic acid at a temperature between about 180° and 230° C. for a time sufficient to carbonize the carbohydrates generally present as an impurity. The heating times naturally depend upon the temperature, but generally are in the range between about 0.5 and about 6 hours. Preferred temperatures are in the range between about 190° and about 225° C.

One variant of our process is to use a single heat treatment. Although this can be applied to the fermentation broth directly, it is preferred that the fermentation broth first be filtered, that salt be removed (most commonly via ion exchange), and the broth be decolorized prior to the heat treatment. Subsequent to the heat treatment the aqueous solution is filtered and decolorized by a decolorizing agent such as activated charcoal.

In another variant two heat treatments are applied to aqueous solutions of lactic acid. Thus, the crude fermentation broth can first be heated followed by filtration, salt removal, and decolorization. The resulting purified lactic acid aqueous solution then can be heated again, filtered, decarbonized, and often given yet a second ion exchange treatment to afford an aqueous solution of purified lactic acid. Concentration may be effected simply by evaporation.

Lactic acid also has been purified by simulated moving bed chromatography as described in U.S. Pat. No. 5,068,418. The feedstock for this separation may be the fermentation broth itself. Consequently, heat treatment may be applied preliminarily to the fermentation broth or, perhaps more efficiently, to the lactic acid isolated by this chromatographic process. In the latter case, the aqueous solution of lactic acid is heated for a time sufficient to carbonize the remaining carbohydrates accompanying lactic acid with subsequent decolorization to remove the formed color bodies to afford a solution of heat-stable lactic acid.

The following examples merely illustrate our invention and are not intended to limit it in any way thereby. Other variants will be apparent to the skilled worker in this area and are intended to be subsumed by the process which is our invention.

EXAMPLE 1

Chromatographic Purification Without Heat Treatment. A 1.4 liter portion of 15 weight percent lactic acid fermentation broth (see Table 1) was filtered through a glass fiber filter. The filtrate was then passed through a series of adsorbent columns: 1) a mixed bed of anion and cation exchange resins; 2) a cation exchange resin (hydrogen form); and 3) activated carbon. The effluent product was concentrated to 88 weight percent. Results of the analysis are shown in Table 1. The majority of cationic species was removed but not the anionic species. The product solution was water white as shown by a 93 APHA color unit measurement. When exposed to heat at 180° C. for 3 hours, the solution turned a dark color. This indicates that trace amounts of color-forming materials (carbohydrate impurities?) are not removed by this method.

EXAMPLE 2

Chromatographic Purification with Single Heat Treatment. A 1.4 liter portion of 15 weight percent lactic acid fermentation broth as used above was subjected to heat treatment at 230° C. for 4 hours. The heated sample was then filtered through a glass fiber filter. The filtrate was passed through a series of adsorbent columns: 1) a mixed bed of anion and cation exchange resins; 2) a cation exchange resin (hydrogen form); 3) an anion exchange resin (hydroxy form); and 4) activated carbon. The effluent product was concentrated to 88 weight percent. Results of the analysis are shown in Table 1. The majority of both anion and cation species were removed. The product solution is water white as shown by a 40 APHA color unit measurement. This product turned to a light yellow color after being heated to 180° C. for 3 hours. This indicates that the majority of carbohydrate impurities were carbonized and removed by this method.

EXAMPLE 3

The product solution from Example 2 was subjected to another heat treatment at 200° C. for 4 hours. The second heated sample was diluted to about 20 weight percent before filtered through a glass fiber filter. The filtrate was passed through an activated carbon column and then concentrated to 88 weight percent. Results of the analysis are shown in Table 1 which is similar to that of Example 2 product. However, no color formation was noticed after the sample was heated to 180° C. for 3 hours. This indicates that all the carbohydrate impurities were carbonized and removed by the second heat treatment.

TABLE 1

| | Analytical Data | | | |
| --- | --- | --- | --- | --- |
| | Lactic Acid Fermentation Booth | Product from Example 1 | Product from Example 2 | Product from Example 3 |
| Lactic Acid (wt. %) | 88 | 88 | 88 | 88 |
| Anionic Species: | | | | |
| phosphate, ppm | 1,115 | 1,080 | trace | trace |
| sulfate, ppm | 763 | 1,100 | trace | trace |
| chloride, ppm | 880 | 1,000 | trace | trace |
| Cationic Species: | | | | |
| Na, ppm | 21.7% | 99 | 41 | 70 |
| K, ppm | 3,810 | <1 | <4 | <2 |
| Fe + Ca + Mg, | 317 | 42 | 7 | 14 |

TABLE 1-continued

| | Analytical Data | | | |
|---|---|---|---|---|
| | Lactic Acid Fermentation Booth | Product from Example 1 | Product from Example 2 | Product from Example 3 |
| ppm APHA Color | 24,200 | 93 | 40 | 48 |

What is claimed is:

1. A process for obtaining heat stable lactic acid from a lactic acid-producing fermentation broth comprising:
   a. filtering and ion-exchanging said fermentation broth;
   b. heating said filtered, ion-exchanged fermentation broth at a pH less than 3 or greater than 8.5 to a temperature between about 180° and 230° C. for a time sufficient to carbonize any dissolved carbohydrates to afford a heat-treated broth;
   c. filtering the heat-treated broth and subjecting the filtrate therefrom to ion-exchange and decolorization to afford an aqueous solution of heat-stable lactic acid; and
   d. isolating the heat-stable lactic acid from said aqueous solution.

2. The process of claim 1 where the heat-treated broth contains between about 8 and about 20 weight percent lactic acid.

3. The process of claim 2 where the heat-treated broth contains between about 10 and about 12 weight percent lactic acid.

4. The process of claim 1 where the temperature is between about 190° and 225° C.

5. A process for obtaining heat-stable lactic acid from a lactic acid-producing fermentation broth comprising subjecting said fermentation broth or a processed fermentation broth to at least one heat treatment at a pH less than 3 or greater than 8.5 at a temperature between about 180° and 230° C. for a time sufficient to carbonize the dissolved carbohydrates.

6. The process of claim 5 where the heat-treated broth contains between about 8 and about 20 weight percent lactic acid.

7. The process of claim 6 where the heat-treated broth contains between about 10 and about 12 weight percent lactic acid.

8. The process of claim 5 where the temperature is between about 190° and 225° C.

9. In a process for isolating lactic acid from a lactic acid-producing fermentation broth, the improvement to produce a heat-stable lactic acid comprising heating an unpurified aqueous solution of lactic acid at a temperature between about 180° and about 230° C. and at a pH less than 3 or greater than 8.5 for a time sufficient to carbonize the carbohydrates dissolved in said aqueous solution, where said aqueous solution is said fermentation broth or a processed fermentation broth.

10. The process of claim 9 where the heat-treated broth contains between about 8 and about 20 weight percent lactic acid.

11. The process of claim 10 where the heat-treated broth contains between about 10 and about 12 weight percent lactic acid.

12. The process of claim 9 where the temperature is between about 190° and 225° C.

* * * * *